(12) United States Patent
Kouwen et al.

(10) Patent No.: US 10,519,516 B2
(45) Date of Patent: Dec. 31, 2019

(54) BACTERIOPHAGE DETECTION

(71) Applicant: DSM IP ASSETS B.V., Heerlen (NL)

(72) Inventors: Roelof Hendrik Matthijs Kouwen, Echt (NL); Douwe Van Sinderen, Echt (NL); Brian McDonnell, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 212 days.

(21) Appl. No.: 15/589,039

(22) Filed: May 8, 2017

(65) Prior Publication Data

US 2017/0327912 A1  Nov. 16, 2017

(30) Foreign Application Priority Data

May 10, 2016 (EP) .................................. 16169020

(51) Int. Cl.
*C12Q 1/70* (2006.01)
*C12N 15/00* (2006.01)

(52) U.S. Cl.
CPC ............... *C12Q 1/701* (2013.01); *C12Q 1/70* (2013.01); *C12Q 2600/158* (2013.01); *C12Q 2600/16* (2013.01)

(58) Field of Classification Search
CPC .... C12Q 1/70; C12Q 1/701; C12Q 2600/158; C12Q 2600/16
See application file for complete search history.

(56) References Cited

FOREIGN PATENT DOCUMENTS

WO    2006/136640 A1    12/2006

OTHER PUBLICATIONS

Qiagen QuantiTect Virus Handbook, pp. 1-72 (Year: 2011).*
del Rio, B. et al., Multiplex Fast Real-Time PCR for Quantitative Detection and Identification of cos- and pac-Type *Streptococcus thermophilus* Bacteriophages, Appl. Env. Microbiol., vol. 74, pp. 4779-4781 (Year: 2008).*
Mills, S. et al., "A new phage on the Mozzarella block: Bacteriophage 5093 shares a low level of homology with otherphages", International Dairy Journal, Jun. 20, 2011, pp. 963-969, vol. 21, No. 12.
Labrie, S. et al., "Complete Genomic Sequence of Bacteriophage ul36: Demonstration of Phage Heterogeneity within the P335 Quasi-Species of Lactococcal Phages", Virology, May 10, 2002, pp. 308-320, vol. 296, No. 2, Elsevier, Amsterdam, Netherlands.
Quiberoni, A. et al., "Diversity of *Streptococcus thermophilus* Phages in a Large-Production Cheese Factory in Argentina", Journal of Dairy Science, Oct. 1, 2006, pp. 3791-3799, vol. 89, No. 10, American Dairy Science Association, U.S.
Guglielmotti, Daniela M. et al., "Genome analysis of two virulent *Streptococcus thermophilus* phages isolated in Argentina", International Journal of Food Microbiology, Nov. 30, 2009, pp. 101-109, vol. 136, No. 1, Elsevier BV, Netherlands.
Le Marrec, Claire et al., "Two groups of bacteriophages infecting *Streptococcus thermophilus* can be distinguished on the basis of mode of packing and genetic determinants for major structural proteins", Applied and Environmental Microbiology, Aug. 1, 1997, pp. 3246-3253.
Lucchini, Sacha et al., "Comparative Genomics of *Streptococcus thermophilus* Phage Species Supports a Modular Evolution Theory", Journal of Virology, Oct. 1, 1999, pp. 8647-8656.
McDonnell, Brian et al., "Identification and Analysis of a Novel Group of Bacteriophages Infecting the Lactic Acid Bacterium *Streptococcus thermophilus*", Applied and Environmental Microbiology, Sep. 1, 2016, pp. 5153-5165, vol. 82, No. 17.
European Search Report of European Patent Application No. 16 16 9020 dated Oct. 26, 2016.

* cited by examiner

Primary Examiner — Teresa E Strzelecka
(74) Attorney, Agent, or Firm — McBee Moore Woodward & Vanik IP, LLC

(57) ABSTRACT

The present invention relates to a kit suitable for detection of *Streptococcus thermophilus* infecting phages, said kit comprising: (a) a first primer pair suitable to generate an amplicon characteristic for a 987 phage; and (b) a second primer pair suitable to generate an amplicon characteristic for a 5093 phage. Further, the present invention relates to a method for detecting the presence of *Streptococcus thermophilus* infecting phages in a sample.

8 Claims, 1 Drawing Sheet

Specification includes a Sequence Listing.

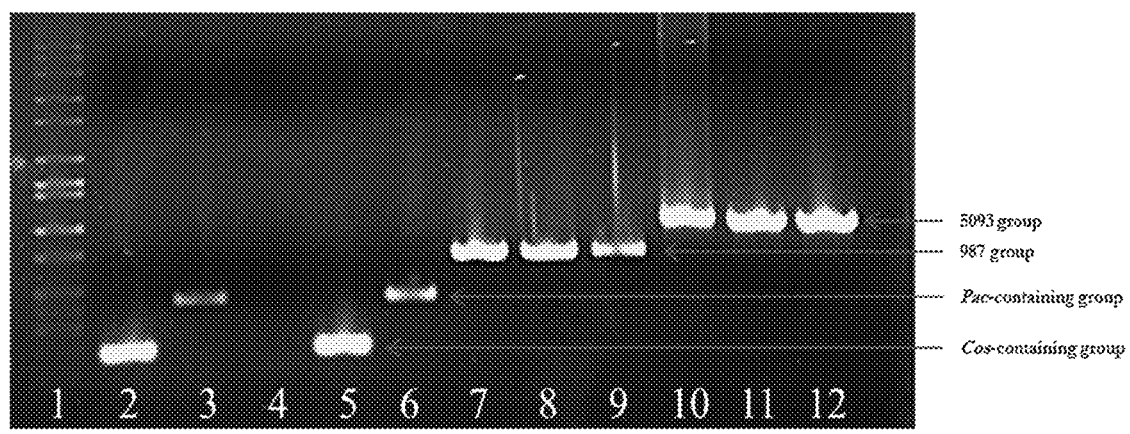

SEQUENCE LISTING

<160> NUMBER OF SEQ ID NOS: 8

<210> SEQ ID NO 1
<211> LENGTH: 21
<212> TYPE: DNA
<213> ORGANISM: Bacteriophage
<220> FEATURE:
<221> NAME/KEY: source
<222> LOCATION: (1)..(21)
<223> OTHER INFORMATION: /organism="bacteriophage" /note="987 Forward primer" /mol_type="unassigned DNA"

<400> SEQUENCE: 1
ctaagcgttt gccactgtca g                                              21

<210> SEQ ID NO 2
<211> LENGTH: 20
<212> TYPE: DNA
<213> ORGANISM: Bacteriophage
<220> FEATURE:
<221> NAME/KEY: source
<222> LOCATION: (1)..(20)
<223> OTHER INFORMATION: /organism="bacteriophage" /note="987 Reverse primer" /mol_type="unassigned DNA"

<400> SEQUENCE: 2
gctgccgctt gtttgaaaac                                                20

<210> SEQ ID NO 3
<211> LENGTH: 20
<212> TYPE: DNA
<213> ORGANISM: Bacteriophage
<220> FEATURE:
<221> NAME/KEY: source
<222> LOCATION: (1)..(20)
<223> OTHER INFORMATION: /organism="bacteriophage" /note="5093 Forward primer" /mol_type="unassigned DNA"

<400> SEQUENCE: 3
ctggctcttg gtggtcttgc                                                20

<210> SEQ ID NO 4
<211> LENGTH: 21
<212> TYPE: DNA
<213> ORGANISM: Bacteriophage
<220> FEATURE:
<221> NAME/KEY: source
<222> LOCATION: (1)..(21)
<223> OTHER INFORMATION: /organism="bacteriophage" /note="5093 Reverse primer" /mol_type="unassigned DNA"

<400> SEQUENCE: 4
gcggcaacca tcttagacca g                                              21

<210> SEQ ID NO 5
<211> LENGTH: 24
<212> TYPE: DNA
<213> ORGANISM: Bacteriophage
<220> FEATURE:
<221> NAME/KEY: source
<222> LOCATION: (1)..(24)
<223> OTHER INFORMATION: /organism="bacteriophage" /note="Cos Forward primer" /mol_type="unassigned DNA"

<400> SEQUENCE: 5
ggttcacgtg tttatgaaaa atgg                                           24

<210> SEQ ID NO 6

```
<211> LENGTH: 24
<212> TYPE: DNA
<213> ORGANISM: Bacteriophage
<220> FEATURE:
<221> NAME/KEY: source
<222> LOCATION: (1)..(24)
<223> OTHER INFORMATION: /organism="bacteriophage" /note="Cos Reverse
      primer" /mol_type="unassigned DNA"

<400> SEQUENCE: 6
agcagaatca gcaagcaagc tgtt                                            24

<210> SEQ ID NO 7
<211> LENGTH: 20
<212> TYPE: DNA
<213> ORGANISM: Bacteriophage
<220> FEATURE:
<221> NAME/KEY: source
<222> LOCATION: (1)..(20)
<223> OTHER INFORMATION: /organism="bacteriophage" /note="Pac Forward
      primer" /mol_type="unassigned DNA"

<400> SEQUENCE: 7
gaagctatgc gtatgcaagt                                                 20

<210> SEQ ID NO 8
<211> LENGTH: 20
<212> TYPE: DNA
<213> ORGANISM: Bacteriophage
<220> FEATURE:
<221> NAME/KEY: source
<222> LOCATION: (1)..(20)
<223> OTHER INFORMATION: /organism="bacteriophage" /note="Pac Reverse
      primer" /mol_type="unassigned DNA"

<400> SEQUENCE: 8
ttagggataa gagtcaagtg                                                 20
```

BACTERIOPHAGE DETECTION

CROSS REFERENCE TO RELATED APPLICATIONS

This application claims priority from EP 16169020.1 filed 10 May 2016, the content of which is incorporated herein by reference in its entirety.

BACKGROUND

Field of the Invention

The present invention relates to a kit suitable for detection of *Streptococcus thermophilus* infecting phages. According to another aspect, the present invention relates to a method for detecting the presence of *Streptococcus thermophilus* infecting phages in a sample. According to yet another aspect the present invention relates to a method for producing a starter culture. According to another aspect the present invention relates to the use for detection of *Streptococcus thermophilus* infecting phages in a sample.

Description of Related Art

*Streptococcus thermophilus* (or *S. thermophilus*) is a lactic acid bacterium which is widely used as a starter culture in the production of fermented milk products (Mora et al. (2002) *Genetic diversity and technological properties of Streptococcus thermophilus strains isolated from dairy products*, J Appl Microbiol 93:2, 278-87). The use of defined *S. thermophilus* starter cultures throughout the 20th century (in accordance with the increased demand for consistency of fermented milk products (Caplice and Fitzgerald (1999) *Food fermentations: role of microorganisms in food production and preservation*, Int J Food Microbiol 50:1-2, 131-49)) has seen a concomitant rise in persistent predation of starter cultures by bacteriophages (or phages) (Garneau and Moineau (2011) *Bacteriophages of lactic acid bacteria and their impact on milk fermentations*, Microb Cell Fact 10 Suppl 1:S20). The presence of phages in the industrial dairy environment fermentations is generally considered to negatively impact on production, with phage infection affecting the rheological and textural properties of the end product (Ma et al. (2015) *Starter culture design to overcome phage infection during yogurt fermentation*, Food Science and Biotechnology 24:2, 521-27).

It has been postulated that the main source of new phages entering a product line is raw milk (Bruttin et al. (1997) *Molecular ecology of Streptococcus thermophilus bacteriophage infections in a cheese factory*, Appl Environ Microbiol 63:8, 3144-50). The first step in the amelioration of this problem is usually the detection and classification of the phages in question (Brussow et al. (1994) *Detection and classification of Streptococcus thermophilus bacteriophages isolated from industrial milk fermentation*, Appl Environ Microbiol 60:12, 4537-43). Phage detection is essential to confirm that fermentation slow-down or failure has indeed been caused by the presence of phages. Furthermore, identification of novel or emerging phages is a crucial step in amelioration of fermentation spoilage, due to the potential need to adjust sanitisation procedures (Binetti and Reinheimer (2000) *Thermal and chemical inactivation of indigenous Streptococcus thermophilus bacteriophages isolated from Argentinian dairy plants*, J Food Prot 63:4, 509-15) and/or BIM generation protocols (Mills et al. (2007) *Efficient method for generation of bacteriophage insensitive mutants of Streptococcus thermophilus yoghurt and mozzarella strains*, J Microbiol Methods 70:1, 159-64) to account for the new phage types.

The classification of bacteriophages infecting *S. thermophilus* into two distinct groups based on their mode of DNA packaging and major structural protein content (Le Marrec et al. (1997) *Two groups of bacteriophages infecting Streptococcus thermophilus can be distinguished on the basis of mode of packaging and genetic determinants for major structural proteins*, Appl Environ Microbiol 63:8, 3246-53) was a major step forward in their characterisation. This knowledge, aided by the sequencing of a number of genomes of *S. thermophilus* phages (Levesque et al. (2005) *Genomic organization and molecular analysis of virulent bacteriophage 2972 infecting an exopolysaccharide-producing Streptococcus thermophilus strain*, Appl Environ Microbiol 71:7, 4057-68), was later used to develop a multiplex PCR methodology enabling the rapid detection of these two groups, namely cos-containing and pac-containing (Quiberoni et al. (2006) *Diversity of Streptococcus thermophilus phages in a large-production cheese factory in Argentina*, J Dairy Sci 89:10, 3791-9). This PCR-based method utilised two primer sets, which were designed on the DNA sequence of the conserved major capsid protein-encoding genes of cos-containing and pac-containing phages. The resultant amplified PCR products are 170 bp (cos-containing phages) and 427 bp (pac-containing phages), and are easily distinguishable when detected by the use of standard DNA visualisation methods.

Further to the cos-containing and pac-containing groups, additional new groups of *S. thermophilus* phages have been identified, namely the '5093 group' and the '987 group'. The '5093 group' was recently described as being highly divergent from both cos-containing and pac-containing phages, particularly in the structural module of the genome (Mills et al. (2011) *A new phage on the 'Mozzarella'block: Bacteriophage 5093 shares a low level of homology with other Streptococcus thermophilus phages*, International Dairy Journal 21:12, 963-69) The genomes of the '987 group' phages exhibit nucleotide identity to phages of the P335 species infecting *Lactococcus lactis*, including ul36 (Labrie and Moineau (2002) *Complete genomic sequence of bacteriophage ul36: demonstration of phage heterogeneity within the P335 quasi-species of lactococcal phages*, Virology 296:2, 308-20), as well as to previously sequenced *S. thermophilus* phages (across the replication module of the genomes).

Considering the apparently rapidly increasing diversity of *S. thermophilus*-infecting phages being present in industrial settings, there is a need in the art for new methods for detection of all four groups of *S. thermophilus* phages.

SUMMARY

The objective of the present invention, amongst other objectives, is to provide kit suitable for the simultaneous detection of *S. thermophilus*-infecting phages.

This objective, amongst other objectives, is met by providing a kit according to the appended claim 1.

Specifically, this objective, amongst other objectives, is met by providing a kit suitable for detection of *Streptococcus thermophilus* infecting phages, said kit comprising:
 (a) a first primer pair suitable to generate an amplicon characteristic for a 987 phage; and
 (b) a second primer pair suitable to generate an amplicon characteristic for a 5093 phage.

In a preferred embodiment, the present kit further comprises:
(c) a third primer pair suitable to generate an amplicon characteristic for a cos phage; and/or
(d) a fourth primer pair suitable to generate an amplicon characteristic for a pac phage.

BRIEF DESCRIPTION OF THE DRAWINGS

FIG. 1 shows Multiplex PCR detection of four groups of S. thermophilus infecting phages as described herein.

DETAILED DESCRIPTION OF A PREFERRED EMBODIMENT

Preferably, the first primer pair comprises a forward primer according to SEQUENCE ID NO: 1 and a reverse primer according to SEQUENCE ID NO: 2, wherein the second primer pair comprises a forward primer according to SEQUENCE ID NO: 3 and a reverse primer according to SEQUENCE ID NO: 4.

Preferably, the third primer pair comprises a forward primer according to SEQUENCE ID NO: 5 and a reverse primer according to SEQUENCE ID NO: 6, wherein the fourth primer pair comprises a forward primer according to SEQUENCE ID NO: 7 and a reverse primer according to SEQUENCE ID NO: 8.

Preferably, the present kit is suitable for detection of four distinct phage groups, preferably chosen from 987 phages, 5093 phages, cos containing phages and pac containing phages.

According to another aspect, the present invention relates to a method for detecting the presence of *Streptococcus thermophilus* infecting phages in a sample, comprising the steps of:
(i) providing a sample;
(ii) performing a PCR analysis of the sample using a first primer pair suitable to generate an amplicon characteristic for a 987 phage and a second primer pair suitable to generate an amplicon characteristic for a 5093 phage.

Preferably, the present method comprises:
(ii) performing a PCR analysis of the sample using a first primer pair suitable to generate an amplicon characteristic for a 987 phage, a second primer pair suitable to generate an amplicon characteristic for a 5093 phage, a third primer pair suitable to generate an amplicon characteristic for a cos phage and a fourth primer pair suitable to generate an amplicon characteristic for a pac phage.

Preferably, the PCR analysis is a multiplex PCR analysis.

Preferably, the first primer pair comprises a forward primer according to SEQUENCE ID NO: 1 and a reverse primer according to SEQUENCE ID NO: 2, wherein the second primer pair comprises a forward primer according to SEQUENCE ID NO: 3 and a reverse primer according to SEQUENCE ID NO: 4.

Preferably, the third primer pair comprises a forward primer according to SEQUENCE ID NO: 5 and a reverse primer according to SEQUENCE ID NO: 6, wherein the fourth primer pair comprises a forward primer according to SEQUENCE ID NO: 7 and a reverse primer according to SEQUENCE ID NO: 8.

Preferably, the present sample is milk or whey.

More preferably, the present method further comprises:
(iii) visualizing the generated amplicons.

According to yet another aspect, the present invention relates to a method for producing a starter culture comprising the present described method for detecting the presence of *Streptococcus thermophilus* infecting phages in a sample and selecting at least one *Streptococcus thermophilus* strain to produce the starter culture.

Preferably, the present at least one *Streptococcus thermophilus* strain is desired in view of susceptibility towards the detected *Streptococcus thermophilus* infecting phages.

According to yet another aspect the present invention relates to the use of the present kit for detection of *Streptococcus thermophilus* infecting phages in a sample.

Definitions

The term "starter" or "starter culture" as used herein refers to a culture of one or more food-grade micro-organisms, in particular lactic acid bacteria, which are responsible for the acidification of the milk base. Starter cultures may be fresh (liquid), frozen or freeze-dried. Freeze dried cultures need to be regenerated before use. For the production of a fermented dairy product, the starter is usually added in an amount from 0.01 to 3%, preferably from 0.01 and 0.02% by weight of the total amount of milk base.

As used herein, the term "lactic acid bacteria" (LAB) or "lactic bacteria" refers to food-grade bacteria producing lactic acid as the major metabolic end-product of carbohydrate fermentation. These bacteria are related by their common metabolic and physiological characteristics and are usually Gram positive, low-GC, acid tolerant, non-sporulating, non-respiring, rod-shaped bacilli or cocci. During the fermentation stage, the consumption of lactose by these bacteria causes the formation of lactic acid, reducing the pH and leading to the formation of a protein coagulum. These bacteria are thus responsible for the acidification of milk and for the texture of the dairy product. As used herein, the term "lactic acid bacteria" or "lactic bacteria" encompasses, but is not limited to, bacteria belonging to the genus of *Lactobacillus* spp., *Bifidobacterium* spp., *Streptococcus* spp., *Lactococcus* spp., such as *Lactobacillus delbruekii* subsp. *bulgaricus*, *Streptococcus salivarius thermophilus*, *Lactobacillus lactis*, *Bifidobacterium animalis*, *Lactococcus lactis*, *Lactobacillus casei*, *Lactobacillus plantarum*, *Lactobacillus helveticus*, *Lactobacillus acidophilus* and *Bifidobacterium breve*.

The term '987 phage' as used in the present context means a phage belonging to the 987 group. A 987 phage can be identified using a primer pair comprising primers according to SEQUENCE ID NO. 1 and 2 as described herein, preferably resulting in an amplicon of 707 bp.

The term '5093 phage' as used in the present context means a phage belonging to the 5093 group. A 5093 phage can be identified using a primer pair comprising primers according to SEQUENCE ID NO. 3 and 4 as described herein, preferably resulting in an amplicon of 983 bp.

The term 'cos phage' as used in the present context means a phage belonging to the cos containing phage group. A cos phage comprises a DNA sequence of the conserved major capsid protein encoding genes which can be amplified using a primer pair comprising primers according to SEQUENCE ID NO. 5 and 6 as described herein, preferably resulting in an amplicon of 170 bp.

The term pac phage as used in the present context means a phage belonging to the pac containing phage group. A pac phage comprises a DNA sequence of the conserved major capsid protein encoding genes which can be amplified using a primer pair comprising primers according to SEQUENCE ID NO. 7 and 8 as described herein, preferably having a resulting amplicon of 427 bp.

The term phage group as used herein is a group of phages which phages share a unique DNA part which allows the identification of phages belonging to the group.

According to a first aspect, the present invention relates to a kit suitable for detection of *Streptococcus thermophilus* infecting phages, said kit comprising:
(a) a first primer pair suitable to generate an amplicon characteristic for a 987 phage; and/or
(b) a second primer pair suitable to generate an amplicon characteristic for a 5093 phage.

The present inventors identified primer pairs that are able to identify the presence of phages belonging to the recently found groups of 987 phags and 5093 phages. This is advantageous since the presence of these phages can now efficiently be identified which allows for rotation of *Streptococcus thermophilus* strains which are less susceptible to the identified phages. The kit allows to analyse samples on the diversity of phages. In this manner, the present kit is useful in methods to analyse industrial milk or whey samples and in case of infection to adequately respond with desired *Streptococcus thermophilus* strains which are less susceptible. Further, the present kit can advantageously be used in methods for the production of custom made starter cultures wherein samples are efficiently analysed on phage content, followed by composing a starter comprising a robust phage rotation to the phages identified. The susceptibility of *Streptococcus thermophilus* strains to the identified phages can be studied by phage host range interaction studies which allows a selection of the desired *Streptococcus thermophilus* strains one a certain phage has been identified.

In a preferred embodiment, the present kit further comprises:
(c) a third primer pair suitable to generate an amplicon characteristic for a cos phage; and/or
(d) a fourth primer pair suitable to generate an amplicon characteristic for a pac phage.

The present kit allows the simultaneous detection of four different groups of phages and is thus a powerful tool for the time efficient analysis of phages in a sample.

Preferably, the first primer pair comprises a forward primer according to SEQUENCE ID NO: 1 and a reverse primer according to SEQUENCE ID NO: 2, wherein the second primer pair comprises a forward primer according to SEQUENCE ID NO: 3 and a reverse primer according to SEQUENCE ID NO: 4. The sequences are shown in table 2 below.

In a preferred embodiment, the present invention relates to a kit suitable for detection of *Streptococcus thermophilus* infecting phages, said kit comprising:
(a) first primer pair comprising a forward primer according to SEQUENCE ID NO: 1 and a reverse primer according to SEQUENCE ID NO: 2; and/or
(b) a second primer pair comprises a forward primer according to SEQUENCE ID NO: 3 and a reverse primer according to SEQUENCE ID NO: 4.

Preferably, the third primer pair comprises a forward primer according to SEQUENCE ID NO: 5 and a reverse primer according to SEQUENCE ID NO: 6, wherein the fourth primer pair comprises a forward primer according to SEQUENCE ID NO: 7 and a reverse primer according to SEQUENCE ID NO: 8. The sequences are shown in table 2 below. Hence, the present kit preferably comprises:
a) first primer pair comprising a forward primer according to SEQUENCE ID NO: 1 and a reverse primer according to SEQUENCE ID NO: 2;
(b) a second primer pair comprises a forward primer according to SEQUENCE ID NO: 3 and a reverse primer according to SEQUENCE ID NO: 4.
(c) third primer pair comprises a forward primer according to SEQUENCE ID NO: 5 and a reverse primer according to SEQUENCE ID NO: 6; and/or
(d) a fourth primer pair comprises a forward primer according to SEQUENCE ID NO: 7 and a reverse primer according to SEQUENCE ID NO: 8

The present primer pairs produce amplicons from 707 bp, 983 bp, 170 bp and 427 bp, respectively. The clear difference in size of these amplicons enables the rapid identification of the four different phage groups.

Therefore, in a preferred embodiment, the present kit is suitable for detection of four distinct phage groups, preferably chosen from 987 phages, 5093 phages, cos containing phages and pac containing phages.

It is further preferred that the present kit is packaged in a manner which allows the storage and shipment of the present primer pairs. In the present kit, the present primer pairs are preferably packaged independently from each other. More preferably, each primer is packaged independently.

Given the efficiency of the present primer pairs in detection of *Streptococcus thermophilus* infecting phages, the present invention relates, according to another aspect, to a method for detecting the presence of *Streptococcus thermophilus* infecting phages in a sample, comprising the steps of:
(i) providing a sample;
(ii) performing a PCR analysis of the sample using a first primer pair suitable to generate an amplicon characteristic for a 987 phage and a second primer pair suitable to generate an amplicon characteristic for a 5093 phage.

Preferably, the present method comprises:
(ii) performing a PCR analysis of the sample using a first primer pair suitable to generate an amplicon characteristic for a 987 phage, a second primer pair suitable to generate an amplicon characteristic for a 5093 phage, a third primer pair suitable to generate an amplicon characteristic for a cos phage and a fourth primer pair suitable to generate an amplicon characteristic for a pac phage.

The present inventors found that the PCR based method allows a rapid detection of phages in a sample, since within a time period of hours the PCR can be performed, while conventional plaque assays to determine phage presence takes at least 48 hours. This benefit of the present invention allows a quicker response time and even implementation at the factory instead of sending samples away to a test lab.

Preferably, the PCR analysis is a multiplex PCR analysis. The present PCR based methods allows the simultaneous detection of phages belonging to the present phage groups.

Preferably, the first primer pair comprises a forward primer according to SEQUENCE ID NO: 1 and a reverse primer according to SEQUENCE ID NO: 2, wherein the second primer pair comprises a forward primer according to SEQUENCE ID NO: 3 and a reverse primer according to SEQUENCE ID NO: 4.

Preferably, the third primer pair comprises a forward primer according to SEQUENCE ID NO: 5 and a reverse primer according to SEQUENCE ID NO: 6, wherein the fourth primer pair comprises a forward primer according to SEQUENCE ID NO: 7 and a reverse primer according to SEQUENCE ID NO: 8.

Preferably, the present sample is milk or whey. The milk can be raw milk but the milk or whey may also be industrial milk or whey samples derived from the milk industry in order to identify *Streptococcus thermophilus* infecting phages in a production line.

Given the clear difference in size of the generated amplicons which allow a rapid identification of the four different phage groups the present method further comprises a step of:

(iii) visualizing the generated amplicons.

Preferably, the present step of visualizing the generated amplicons comprises standard DNA visualisation methods, such as preferably gel electrophoresis.

Given the advantages of the present PCR based kit and method for producing starter cultures, the present invention relates, according to yet another aspect, to a method for producing a starter culture comprising the present described method for detecting the presence of *Streptococcus thermophilus* infecting phages in a sample and selecting at least one *Streptococcus thermophilus* strain to produce the starter culture.

Preferably, the present at least one *Streptococcus thermophilus* strain is desired in view of susceptibility towards the detected *Streptococcus thermophilus* infecting phages. Based on knowledge of the susceptibility of *Streptococcus thermophilus* strains towards phages from the groups of 987 phages, 5093 phages, cos containing phages and pac containing phages, the present method allows an efficient selection of strains which provide a robust rotation scheme towards the identified phages. Once a strain is known as host for 987 or 5093 phages, the present invention allows to detect the presence of these phages in a sample and if detected subsequently to select other *Streptococcus thermophilus* strains which are not a host for 987 or 5093 phages.

According to yet another aspect the present invention relates to the use of the present kit for detection of *Streptococcus thermophilus* infecting phages, preferably for detection of *Streptococcus thermophilus* infecting phages in a sample. More specifically, the present invention relates to the use of the present kit for detection of *Streptococcus thermophilus* infecting phages belonging to the 987 phages, 5093 phages, cos containing phages and/or pac containing phages.

FIGURE LEGEND

FIG. 1:

Multiplex PCR detection of four groups of *S. thermophilus* infecting phages using the primers described in Table 2. Lane 1: Full scale 1 kb DNA Marker (Fisher Scientific), L2: 7201 (cos-containing control), L3: O1205 (pac-containing control), L4: negative control (sterile distilled $H_2O$), L5: 9851 (cos-containing control), L6: 9853 (pac-containing control), L7-9: 987 group phages 9871, 9872 and 9873, L10-12: 5093 group phages 0093, 0094 and 0095.

The present invention is further illustrated in a non limiting example.

EXAMPLES

Materials and Methods

1. Bacterial Growth and Storage Conditions

The bacterial strains and bacteriophage isolates applied in this example are listed in Table 1. *S. thermophilus* strains were routinely grown from single colonies or 20% reconstituted skimmed milk (RSM) stocks in M17 broth (Oxoid, Hampshire, U.K.) supplemented with 0.5% lactose (Sigma-Aldrich, St. Louis, Mo., U.S.A.).

TABLE 1

Bacterial strains and bacteriophages applied.

| Bacteria/Phage | Description | Source |
|---|---|---|
| Bacterial strain | | |
| *S. thermophilus* ST67009 | *S. thermophilus* industrial starter | DSM, Delft, The Netherlands |
| *S. thermophilus* ST64987 | " | " |
| *S. thermophilus* ST64985 | " | " |
| *S. thermophilus* 1205.3 | " | UCC, Cork, Ireland |
| *S. thermophilus* B106 | " | " |
| Bacteriophage | | |
| O1205 | Temperate phage infecting 1205.3 | UCC, Cork, Ireland |
| 7201 | Lytic phage infecting B106 | " |
| 9851 | Lytic phage infecting ST64985 | DSM, Delft, The Netherlands |
| 9853 | " | " |
| 9871 | Lytic phage infecting ST64987 | " |
| 9872 | " | " |
| 9873 | " | " |
| 0093 | Lytic phage infecting ST67009 | " |
| 0094 | " | " |
| 0095 | " | " |

2. Bacteriophage Propagation, Enumeration and Storage Conditions

Whey samples sourced from dairy processing plants were analysed for the presence of phages using spot assay and plaque assay tests (Lillehaug (1997) *An improved plaque assay for poor plaque-producing temperate lactococcal bacteriophages*, J Appl Microbiol 83:1, 85-90), whereby LM17 broth (as above) was supplemented with 0.25% glycine and either 10 g/L (solid agar base) or 4 g/L (semi-solid overlay) technical agar (VWR Chemicals, Radnor, Pa., U.S.A.). Single plaques were propagated on their appropriate host strain (at least twice to ensure pure phage preparations) according to the method of Moineau et al. ((1994) *Evolution of a Lytic Bacteriophage via DNA Acquisition from the Lactococcus lactis Chromosome*, Appl Environ Microbiol 60:6, 1832-41). Resultant lysates were filtered (0.45 μm; Sarstedt, Nümbrecht, Germany) and stored at 4° C. for use in subsequent assays.

3. Phage Genomic DNA Preparation

Phage DNA was prepared using a method adapted from (Moineau, Pandian (1994) *Evolution of a Lytic Bacteriophage via DNA Acquisition from the Lactococcus lactis Chromosome*, Appl Environ Microbiol 60:6, 1832-41). Briefly, 20 μl proteinase K (20 mg/ml; Fisher Scientific, Hampton, N.H., U.S.A.) was added to approximately 200 μl (phage titer-dependent) CsCl purified phage, or to 500 μl Polyethylene glycol (PEG; Sigma-Aldrich) precipitated phage lysate, and the mixture placed at 56° C. for 20 minutes. Sodium dodecyl sulphate solution (SDS; Sigma Aldrich) was added to a final concentration of 1-1.5% before heating at 65° C. for 30 mins. Potassium acetate was added to a final concentration of 1 M and the mixture placed on ice for 30 mins. Centrifugation at 13,200×g was followed by phenol chloroform:isoamyl alcohol (25:24:1; Sigma Aldrich) extraction and the addition of 0.1 volume of 3 M sodium acetate and 2.5 volumes of ice cold 96% ethanol (Sigma Aldrich). Precipitated phage DNA was pelleted at 21,000×g and resuspended in 50 μl TE buffer (10 mM Tris-HCl, 1 mM EDTA, pH 7.5). Total genomic DNA was qualitatively analysed by electrophoretic examination using a 1% agarose (Sigma-Aldrich) gel, on which the samples were separated at 100 V for at least 20 minutes.

4. PCR Detection of Distinct Phage Groups

The primers applied in the detection of cos-containing, pac-containing, 5093 and 987 phages groups are shown in Table 2. Primers enabling the detection of the 987 groups were designed based on the nucleotide sequence of a conserved scaffolding protein-encoding $ORF6_{9871}$ gene, which is located within the structural module of the genomes of the four known phages belonging to this group. 5093 group primers were designed using the nucleotide sequence of a portal protein-encoding $ORF3_{0095}$ gene, also conserved in other members of this group.

(Qiagen, Hilden, Germany). Each PCR reaction contained 1 μl of each of the eight primers listed in Table 2. PCR conditions were as follows: Initial denaturation of 95° C. for 2 minutes, 30 cycles of 95° C. for 15 seconds, 55° C. for 30 sec and 72° C. for 1 min, with a final extension of 72° C. for 10 min. Amplified PCR products were visualised on a 1% agarose (Sigma-Aldrich) gel.

Example 1

1. Detection of cos-Containing, pac-Containing, 987 Group and 5093 Group Phages

The bacterial strains and phages applied in this study are listed in Table 1. The genomic DNA of two cos-containing, two pac-containing, and six novel phages (three of each belonging to the 987 and 5093 groups, respectively), were selected for multiplex PCR typing. These individual phage isolates are genetically distinct between groupings (particularly across the structural modules) as well as within groupings (predominantly across the lysis, lysogeny and replication genomic modules). A high level of nucleotide identity (>90%) was observed across the structural modules of those phages that are members of the same group. Previously, the conserved (i.e., structural protein-encoding gene containing) regions of cos-containing and pac-containing were exploited during primer design to enable the detection of these distinct phage groups (Guglielmotti et al. (2009) *Genome analysis of two virulent Streptococcus thermophilus phages isolated in Argentina*, Int J Food Microbiol 136:1, 101-9). A similar approach was adopted for the purpose of detecting members belonging to the 5093 and 987 group phages, as detailed in the materials and methods.

The genomic DNA of two previously described cos-containing and pac-containing phages (O1205 and 7201) as well as two phages whose genomes have been sequenced (9851 and 9853; mentioned above) were subjected to an identical PCR amplification to illustrate the size difference between products amplified using previously described cos-containing and pac-containing PCR primer sets (FIG. 1, lanes 2, 3, 5 and 6) and those described in the present context (FIG. 1, lanes 7-12). The clear difference in size of these PCR products (Table 2) enables the rapid identification of four distinct groups of phages infecting *S. thermophilus*,

TABLE 2

PCR primers.

| SEQ ID No. | Primer | Sequence (5'-3') | Target phage group | Product size (bp) |
|---|---|---|---|---|
| 1 | 987F | CTAAGCGTTTGCCACTGTCAG | 987 | 707 |
| 2 | 987R | GCTGCCGCTTGTTTGAAAAC | 987 | |
| 3 | 5093F | CTGGCTCTTGGTGGTCTTGC | 5093 | 983 |
| 4 | 5093R | GCGGCAACCATCTTAGACCAG | 5093 | |
| 5 | CosF | GGTTCACGTGTTTATGAAAAATGG | cos-containing | 170 |
| 6 | CosR | AGCAGAATCAGCAAGCAAGCTGTT | cos-containing | |
| 7 | PacF | GAAGCTATGCGTATGCAAGT | pac-containing | 427 |
| 8 | PacR | TTAGGGATAAGAGTCAAGTG | pac-containing | |

PCR reactions were carried out using freshly isolated phage DNA as template in a total volume of 25 μl utilising Taq polymerase, according to manufacturer's instructions even when the phage isolates within the specific groups are genetically distinct. This size difference also enables simultaneous detection of all four groups.

The invention claimed is:

1. A method for detecting the presence of *Streptococcus thermophilus* infecting phages in a sample, comprising
   (i) providing a sample; and
   (ii) performing a multiplex PCR analysis of the sample using a first primer pair suitable to generate an amplicon from nucleic acid sequences in a 987 phage and a second primer pair suitable to generate an amplicon from nucleic acid sequences in a 5093 phage,
      wherein the first primer pair comprises the forward primer comprising the nucleotide sequence of SEQ ID NO: 1 and the reverse primer comprising the nucleotide sequence of SEQ ID NO: 2, and wherein said 987 phage amplicon is 707 base pairs in length;
      and wherein the second primer pair comprises the forward primer comprising the nucleotide sequence of in SEQ ID NO: 3 and the reverse primer comprising the nucleotide sequence of SEQ ID NO: 4, and wherein said 5093 phage amplicon is 983 base pairs in length.

2. The method according to claim 1, wherein step (ii) comprises performing a PCR analysis of the sample using a first and a second primer pair set according to claim 1, a third primer pair suitable to generate an amplicon from nucleic acid sequences of a cos phage, and a fourth primer pair suitable to generate an amplicon from nucleic acid sequences of a pac phage,
   wherein the third primer pair comprises the forward primer comprising the nucleotide sequence of SEQ ID NO: 5 and the reverse primer comprising the nucleotide sequence of SEQ ID NO: 6, and wherein said cos amplicon is 170 base pairs in length;
   and the fourth primer pair comprises the forward primer comprising the nucleotide sequence of set forth in SEQ ID NO: 7 and the reverse primer comprising the nucleotide sequence of SEQ ID NO: 8, and wherein said pac amplicon is 427 base pairs in length.

3. The method according to claim 1, wherein the sample is milk or whey.

4. The method according to claim 1, further comprising:
   (iii) visualizing the generated amplicons.

5. A method for producing a starter culture comprising applying the method according to claim 1 to one or more candidate *Streptococcus thermophilus* strains and selecting at least one *Streptococcus thermophilus* strain to produce the starter culture, wherein the selected strain(s) for the starter culture are less susceptible to one or more of any phage identified according to claim 1.

6. A method for detecting the presence of *Streptococcus thermophilus* infecting phages in a sample, comprising
   (i) providing a sample; and
   (ii) performing a multiplex PCR analysis of the sample using a first primer pair suitable to generate an amplicon from nucleic acid sequences in a 987 phage and a second primer pair suitable to generate an amplicon from nucleic acid sequences in a 5093 phage, wherein said first primer pair is specific for the nucleotide sequence of the conserved scaffolding protein-encoding ORF6$_{9871}$ gene and wherein said second primer pair is specific for the nucleotide sequence of the portal protein-encoding ORF3$_{0095}$ gene.

7. The method according to claim 1, wherein the first primer pair comprises of the forward primer consisting of the nucleotide sequence of SEQ ID NO: 1 and the reverse primer consisting of the nucleotide sequence of SEQ ID NO: 2, and wherein said 987 phage amplicon is 707 base pairs in length;

and wherein the second primer pair comprises the forward primer consisting of the nucleotide sequence of in SEQ ID NO: 3 and the reverse primer consisting of the nucleotide sequence of SEQ ID NO: 4, and wherein said 5093 phage amplicon is 983 base pairs in length.

8. The method according to claim 2, wherein the third primer pair comprises the forward primer consisting of the nucleotide sequence of SEQ ID NO: 5 and the reverse primer consisting of the nucleotide sequence of SEQ ID NO: 6, and wherein said cos amplicon is 170 base pairs in length;

and the fourth primer pair comprises the forward primer consisting of the nucleotide sequence of SEQ ID NO: 7 and the reverse primer consisting of the nucleotide sequence of SEQ ID NO: 8, and wherein said pac amplicon is 427 base pairs in length.

* * * * *